US008155411B2

(12) United States Patent
Hof et al.

(10) Patent No.: US 8,155,411 B2
(45) Date of Patent: Apr. 10, 2012

(54) METHOD, APPARATUS AND COMPUTER PROGRAM FOR QUANTITATIVE BIFURCATION ANALYSIS IN 3D USING MULTIPLE 2D ANGIOGRAPHIC IMAGES

(75) Inventors: Jacobus Adrianus Engelbertus Johannes Hof, Kerkrade (NL); Bas Weijers, Maasmechelen (BE); Jean-Paul Michel Maria Aben, Limbricht (NL); Coenraad Christiaan Albert Lokkerbol, Maastricht (NL)

(73) Assignee: Pie Medical Imaging B.V., Maastright (NL)

( * ) Notice: Subject to any disclaimer, the term of this patent is extended or adjusted under 35 U.S.C. 154(b) by 931 days.

(21) Appl. No.: 12/177,850

(22) Filed: Jul. 22, 2008

(65) Prior Publication Data

US 2010/0021025 A1 Jan. 28, 2010

(51) Int. Cl.
 *G06K 9/00* (2006.01)
(52) U.S. Cl. ........................................ 382/128
(58) Field of Classification Search .................. 382/128, 382/131
 See application file for complete search history.

(56) References Cited

U.S. PATENT DOCUMENTS

| | | | |
|---|---|---|---|
| 6,301,498 B1 * | 10/2001 | Greenberg et al. | 600/425 |
| 2003/0208116 A1 * | 11/2003 | Liang et al. | 600/407 |
| 2009/0060298 A1 * | 3/2009 | Weijers et al. | 382/128 |
| 2010/0016658 A1 * | 1/2010 | Zou et al. | 600/101 |

OTHER PUBLICATIONS

E. Bullitt, G. Gerig, S. M. Pizer, W. Lin, and S. R. Aylward, "Measuring Tortuosity of the Intracerebral Vasculature from MRA Images", IEEE-TMI 22: 1163-1171, 2003.*

U.S. Appl. No. 11/845,154, filed Aug. 27, 2007, Weijers, Bas.
Goktekin, Omer et al., A New Quantitative Analysis System for the Evaluation of Coronary Bifurcation Lesions, Catheterization and Cardiovascular Interventions, 2007 69:172-180.
Gronenschild, Ed, et al., CAAS II: A Second Generation System for Off-Line and On-Line Quantitative Coronary Angiography, Catheterization and Cardiovascular Diagnosis 1994 33: 61-75 (1994).
Wahle, Andreas, et al., 3D Heart-Vessel Reconstruction form Biplane Angiograms,IEEE Computer Graphics and Applications Jan. 1996, 16:1 pp. 65-73, German Heart Institute Berlin.
Bullitt, Elizabeth, et al., Measuring Tortuosity of the Intracerebral Vasculature from MRA Images, close variant of this paper published in IEEE-TMI, 2003 22:1163-1171.
Hart, William E. et al., Automated measurement of retinal vascular tortuosity.
Cormen, Thomas H. et al., Introduction to Algorithms, 1998, pp. 527-532, The MIT Press, Cambridge, Massachusetts, USA.

* cited by examiner

*Primary Examiner* — Clayton E Laballe
*Assistant Examiner* — Noam Reisner
(74) *Attorney, Agent, or Firm* — Gordon & Jacobson, PC

(57) ABSTRACT

A computer-implemented method (and corresponding data processing facility and computer program) for creating a 3D bifurcation healthy model from multiple 2D angiographic images comprises the following:
 a. Creating a 3-D model based on said images;
 b. Defining a bifurcation region regarding said 3D model;
 c. Creating an area curve regarding said region;
 d. Creating a reference area curve regarding said region whilst reconstructing in 2D;
 e. Creating a healthy model regarding said area curves; and
 f. Computing quantitative analysis results regarding said healthy model based on the healthy cross-sectional areas of the bifurcation, obstruction boundaries and the diseased 3D model consisting of the bifurcation centerlines and cross-sections of the lumen on the centerline, the healthy centerline and cross-sections.

17 Claims, 6 Drawing Sheets

1a

1b

1c 3a  3b 4a  4b  4c 5a                    5b

5c

METHOD, APPARATUS AND COMPUTER PROGRAM FOR QUANTITATIVE BIFURCATION ANALYSIS IN 3D USING MULTIPLE 2D ANGIOGRAPHIC IMAGES

BACKGROUND OF THE INVENTION

1. Field of the Invention

The present invention relates to a method and apparatus for accurately defining a healthy cross-section area function for quantitative three-dimensional (3D) analysis using in particular multiple angiographic images.

2. State of the Art

Angiography, in particular coronary angiography, refers to the process of investigating coronary arteries to determine the severity of any narrowing that may exist, such as by finding stenotic arteries. Quantitative Coronary Analysis (QCA) of single arteries has become a standard for guiding interventions and executing trail studies in coronary revascularization. However, angiographic analysis of lesions in or near a bifurcation presents a considerable problem since QCA for single arteries cannot handle more complex geometries. The definition of bifurcation herein is a splitting of a main tubular artery into two or more further tubular arteries. For example, the left coronary artery bifurcates into the left anterior descending artery and the left circumflex artery.

QCA of a bifurcation involves automatic segmentation of the bifurcation. This can be followed by reconstructing a healthy state that includes the bifurcation area itself. The reference artery diameter, which means the artery's healthy diameter as computed by the QCA, is typically based on averages of the artery "normal" parts before and after the bifurcation, respectively. So the greatest challenge for bifurcation lesion analysis is extracting the true reference artery size of both the proximal artery and its side branches. Conventional QCA reconstructs the healthy artery by assuming minimal artery tapering and cannot handle large steps in diameter that are caused by the bifurcation itself. Furthermore, conventional QCA focuses on 2D quantitative analysis which is sensitive for out-of-plane calibration errors and foreshortening. Foreshortening is a well known phenomenon in quantitative analysis of x-ray images, caused by the fact that x-ray may be seen as a shadow image.

Most conventional QCA methods allow inputting a user-defined reference, which could eliminate the wrong reference definition. However, this reference diameter, and area in case of 3D, would still only be valid on the one side of the bifurcation where the user defined the reference. This option is furthermore little reproducible such as through operator inaccuracy and subjectivity.

Currently no detailed publication has solved the above limitations. O. Goktekin et al, "A new quantitative analysis system for the evaluation of coronary bifurcation lesions: Comparison with current conventional methods", Catheterization and Cardiovascular Interventions 69:172-180 (2007), evaluates a bifurcation package, in which the bifurcation is divided into three parts on each of which conventional QCA is applied. Goktekin describes a method for solving the reference problem by eliminating the central bifurcation region from the reference calculations. Therefore, the central bifurcation is still left out of consideration, both for calculating the artery diameter, and also for definition of the artery reference diameter. Furthermore, the method fully focuses on 2D quantitative bifurcation analysis.

U.S. patent application Ser. No. 11/845,154 describes a method to solve the reference problem, but only for 2D quantitative bifurcation analysis. In the present invention the artery reference, which is in 3D expressed in cross-sectional area function is presented. By using 3D information, errors in artery dimension caused by foreshortening and out-of-plane calibration are eliminated. Also the size of the artery along the length of the selected artery segment is expressed in cross-sectional area instead of diameters.

Furthermore in the disclosure hereinafter, several medical terms, such as stenosis, plaque, obstruction and lesion, are used to indicate various medical aspects of a diseased vessel of which ultimately the size must be calculated, without such medical aspects relating to the technical steps and apparatus of the invention.

SUMMARY OF THE INVENTION

It is therefore an object of the invention to extend prior art to provide a more accurate and reproducible method and system for determining the healthy cross-sectional area function for a quantitative bifurcation analysis in 3D by using in particular multiple angiographic images. Based on the diseased 3D bifurcation model, which is computed from multiple 2D angiographic images, a reconstruction of the cross-sectional area function is computed as representing the cross-sectional area of a healthy artery.

In short, a 3D quantitative bifurcation analysis consists of the following steps:
1. Creating a 3D bifurcation model from multiple 2D angiographic images (for example, employing the methodology described in Whale, Oswald, Fleck, "3D Heart-Vessel reconstruction from biplane angiograms", IEEE Computer Graphics And Applications Vol. 16, No. 1, January 1996 pp. 65-73, herein incorporated by reference in its entirety). An example is shown in FIGS. 1a and 1b.
2. Determining the cross-sectional area for each position in the 3D model (by combining the diameter measurements from the 2D images using the same approach as introduced in this invention for the reference area function).
3. Creation of the healthy cross-sectional area function (i.e., the cross-sectional area per position on the 3D model if no obstruction would be present).
4. Creation of the healthy 3D bifurcation model of the diseased region.
5. Determining quantitative analysis results (for example, by using the 3D equivalent diameter in a 2D bifurcation analysis as introduced in U.S. application Ser. No. 11/845,154, herein incorporated by reference in its entirety).

The object of the invention is realized according to the invention by methodology for quantitative analysis on medical image data of a bifurcated tubular organ. The method makes it possible to automatically reconstruct the non-diseased bifurcation and to determine important plaque related quantitative analysis results like, but not limited to, obstruction amount, plaque extent, plaque dimensions, healthy artery diameter and related results thereby providing an improved tool for a surgeon to select in clinical practice a suitable surgical part or device such as a stent or a dottering element.

BRIEF DESCRIPTION OF THE DRAWINGS

Now, the invention will hereinafter be discussed with reference to the detailed disclosure hereinafter of the preferred embodiment, and more in particular with reference to the Figures that illustrate:

FIGS. 1a and 1b are two respective two-dimensional (2D) image projections generated from a three-dimensional (3D) angiography that is produced from an exemplary arterial geography illustrated by FIG. 1c; notably the latter shows the generally 3D character of the bifurcation; note that additional projections could have been used;

FIG. 2a is a schematic illustration of a bifurcation with reference diameters (dotted) for the three arteries that are connected at the bifurcation, such as found through an interpolated local reference method for each individual artery; note the vessel volumes as shown and hatched item 50 representing a partial obstruction;

FIGS. 2b1 and 2b2 are schematic illustrations of a bifurcation with 3D reference diameters used in the 2D images to reconstruct the healthy arteries outside the bifurcation proper (bold dotted lines); in FIG. 2b1, the obstruction 50a shows up, whereas it is obscured in FIG. 2b2;

FIGS. 2c1 and 2c2 are schematic illustrations of the bifurcation of FIGS. 2b1 and 2b2, where the complete bifurcation region is reconstructed in the respective 2D images as shown in bold continuous bold lines;

FIG. 2d is a schematic illustration of a 3D reconstruction (fat lines) of the 2D bifurcation reconstruction of FIGS. 2c1 and 2c2; note that the obstruction reconstruction 50b is also shown;

FIG. 4a is a schematic illustration of an exemplary 2D bifurcation similar to FIG. 3a;

FIG. 4b is a schematic illustration wherein the 2D bifurcation of FIG. 4a is split into a main and side branch vessels through dotted contours 52, 54;

FIG. 4c is a schematic illustration wherein the main and side branch vessels defined in FIG. 4b are split into respective separate entities entities by cutting off the other branch at dotted edge 52 for the left branch and at dotted edge 54 for the right branch;

DETAILED DESCRIPTION OF THE PREFERRED EMBODIMENT

For purposes of description herein, the following terms are defined as follows:

a "polyline" is a listed sequence of straight line segments;

"equivalent diameter" is the diameter of the circle with the same area as the artery cross-section;

"proximal" is an anatomical term meaning the side of the artery or vein from which the blood comes; an example is the proximal side of an artery is the side closest to the heart;

"distal" is an anatomical term meaning the side of the artery or vein where the blood flows to; an example is the distal side of an artery is the side furthest from the heart;

"lumen" is an anatomical term meaning the interior of an artery or vein through which blood flows;

"Pob" or "point of bifurcation" is the point at which the centerlines of three branches coincide;

"Sob" or "start of bifurcation" is the proximal ostium;

"Eob" or "end of bifurcation" is the distal ostium of a branch;

"main branch" is an anatomical term meaning the proximal vessel portion in addition to the largest of the two distal arteries connected at the bifurcation;

"side branch" is an anatomical term meaning the proximal vessel portion in addition to the smallest of the two distal arteries connected at the bifurcation; and "over projection" shall mean vessels that appear mutually superimposed in a 2D image projection.

Figure 7:
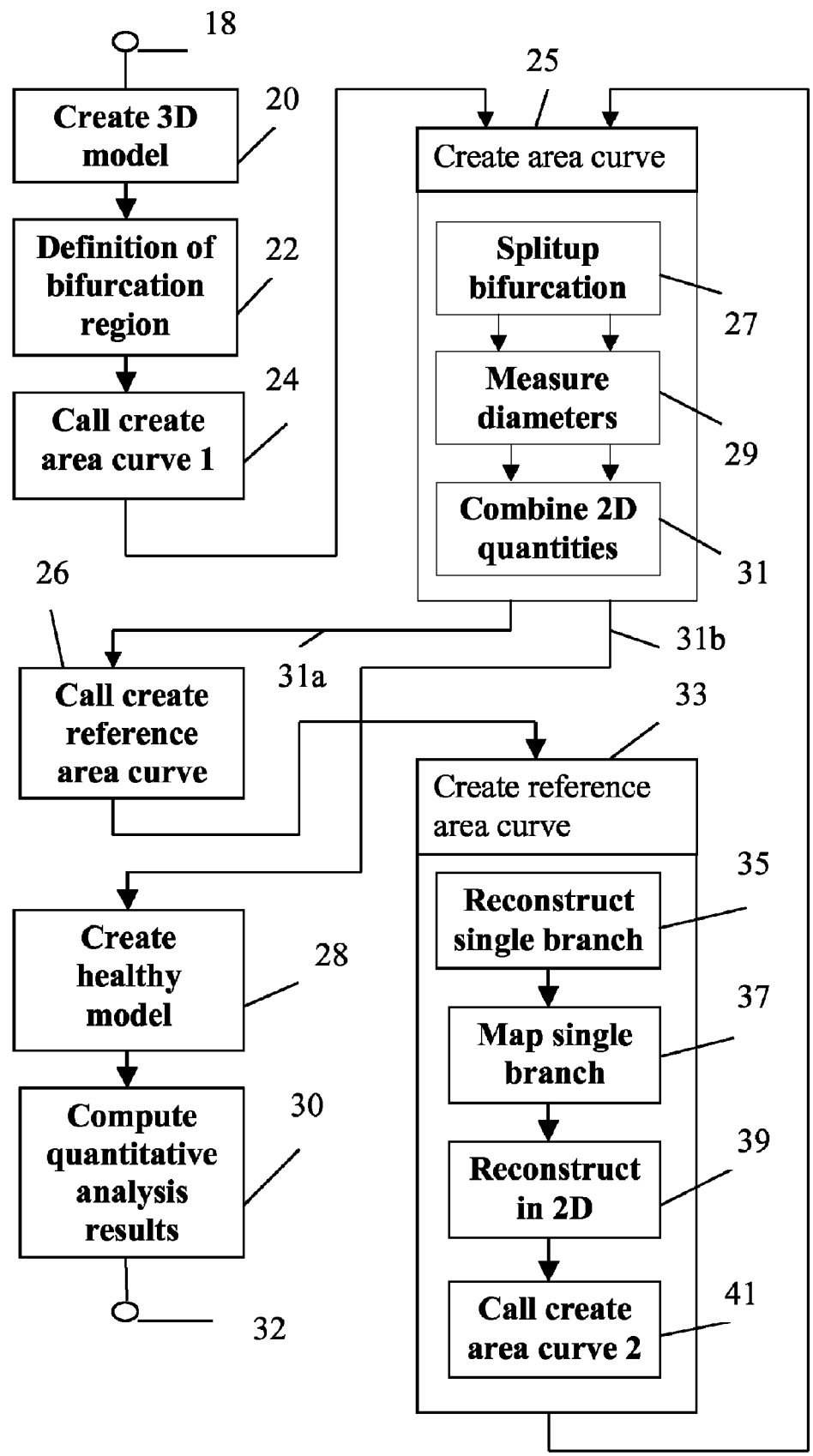
FIG. 7 is a flow chart for performing a quantitative 3D bifurcation analysis in accordance with the present invention.

FIG. 7 illustrates a flow diagram for performing a quantitative 3D bifurcation analysis in accordance with the present invention Various references to the Figures are given. Hereinafter each of the blocks in the diagram will be explained in detail. The method of the present invention is preferably carried out by a data processing facility such as a computer workstation that includes a data processing platform (e.g., CPU, memory system, non-volatile storage, display adapter) that interfaces to user input devices (such as a keyboard and pointing device) and one or more display devices and/or printer for user output. The methodology of the present invention is preferably realized as a software application that is stored on one or more optical discs (or other form of non-volatile memory), or possibly downloaded from a remote computer system, and loaded onto the data processing platform for execution thereon.

Prior art teaches the creation of the 3D model as represented by block 20 of FIG. 7 that gets its input data via notional terminal 18. Briefly, a typical 3D model can be created as follows. The 3D bifurcation model will be created using two or more 2D acquisitions of the bifurcation taken from different view points. Within each angiographic image the bifurcation is detected by using an automatic segmentation algorithm. Here it is assumed that the 2D bifurcation segmentation at least comprises the lumen contours, end-of-bifurcation definition, the 2D lumen centerline and 2D diameter curves along the detected vessel. An example of such segmentation algorithm is described in U.S. patent application Ser. No. 11/845,154, of record. The detected 2D bifurcation is then divided into two single arteries, the main-branch and the side-branch. The main-branch is defined as the artery part covering proximal to distal 1, and the side-branch is defined as the artery part covering proximal to distal 2.

First all main-branches of the 2D projections are used to create the main branch centerline in 3D. The same is done for the side branch. Using the lumen wall contours from the 2D acquisitions, the 3D cross-sectional contours can be created of both the main and side branch in 3D. An example of such processing is described in Whale, Oswald, Fleck, "3D Heart-Vessel reconstruction from biplane angiograms", IEEE Computer Graphics And Applications Vol. 16, No. 1, January 1996 pp. 65-73, incorporated by reference above in its entirety.

Block 22 of FIG. 7 shows the defining of the bifurcation region. In particular, after the 3D model definition of block 20, the bifurcation region is bounded between the start of bifurcation (sob) and the end of bifurcation (eob).

The start of bifurcation is at the point at which the main-branch and side-branch do not coincide anymore at the proximal side.

The location at which the main and side branch model do not intersect anymore at the distal side is called the end of bifurcation (of the distal1 and distal2 artery). The computation of the location at which the models of the 2 branches do not intersect anymore is mathematically a trivial problem, given the 3D model.

Now we describe the creation of the cross-sectional area curve in block 25 of FIG. 7 which is specified further by sub-blocks 27, 29, 31. Block 25 is entered from block 22 through the call create area curve 1 block 24. For the cross-sectional area computation, the 2D bifurcation segmentations results are used. First the 2D measurements are corrected for out-of-plane calibration errors and foreshortening as known by the 3D model.

Figure 3:
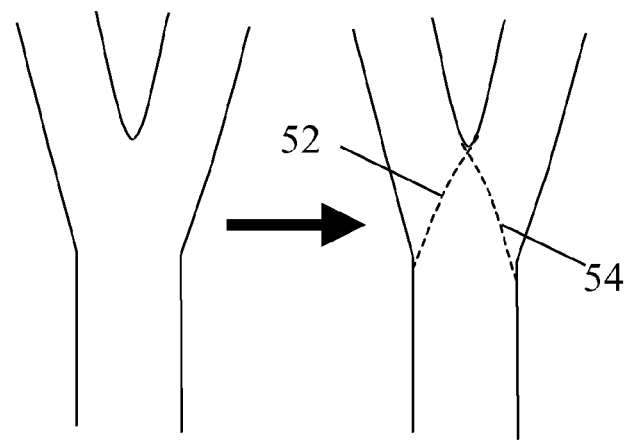
FIG. 3a is a schematic illustration of an exemplary 2D bifurcation.
FIG. 3b is a schematic illustration wherein the 2D bifurcation of FIG. 3a is split into a main and side branch vessels through dotted contours 52, 54.
Figure 4:
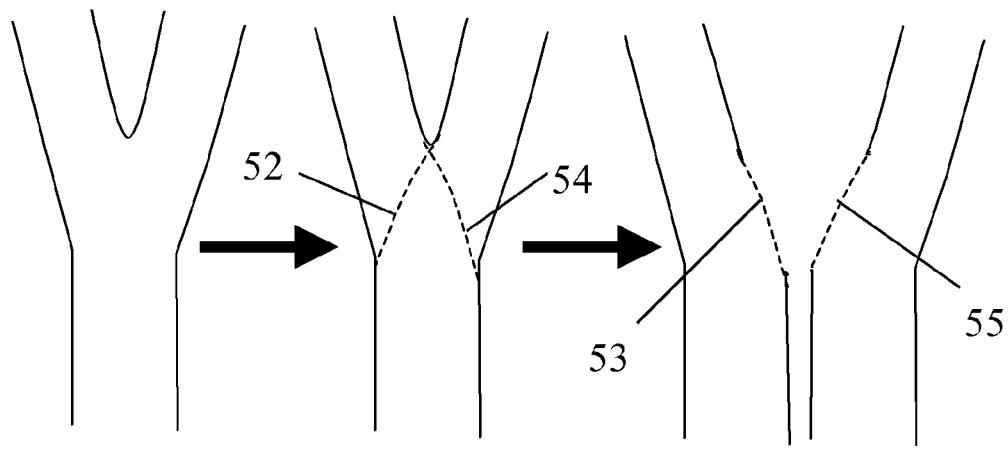

To use the 2D measurements as corrected according to the 3D information, we must first eliminate any partly obscured bifurcation (over projection) in one or more of the image projections. This is block 27 of FIG. 7. This is done by converting the 2D bifurcation into a main branch and a side branch by properly defining virtual edges 52, 54 for the two branches that divide the bifurcation (see dotted lines 52, 54 in FIG. 3*b*). This results in two merged vessels, one for the main branch and one for the side branch (see FIG. 3). The merged vessel is created as follows: the bifurcation detection (and reconstruction) is split up into a main and side branch by properly defining virtual edges that divide the bifurcation, see FIG. 4 with virtual edges 53, 55.

These virtual edges start at the 2D centerline position that corresponds to the 3D start of bifurcation and end at the 2D end of bifurcation points of the distal1 and distal2 artery as described in U.S. patent application Ser. No. 11/845,154, incorporated by reference above in its entirety. The diameters of the 2D merged branches are then computed (block 29 of FIG. 7). Here, we only describe the creation of the merged vessel for the main branch. The creation of the merged vessel for the side branch is similar.

We start by recreating the 2D centerline between the 2D centerline position (sob2D) that corresponds to the 3D start of bifurcation and the 2D end of the bifurcation (eob) of the first distal artery. The recreated 2D centerline is a spline. It is defined by four control nodes on the 2D bifurcation centerline:

a node at the sob2D centerline point a node at the local radius more proximal that 2D centerline position a node at the 2D eob a node at the local artery radius more distal than the 2D eob The spline will be interpolated such that it has the same number of samples as the original 2D bifurcation centerline.

Between the sob2D and 2D eob of the first distal artery a contour (virtual edge) is now defined through the bifurcation using the merged 2D centerline (an example is the contour depicted by the dotted line 53 or 55 in FIG. 4*c*). At sample i of the 2D centerline the contour will be placed at distance r(i) perpendicular to the merged 2D centerline. Here r(i) is a linear function such that r(sob2D) equals the bifurcation radius at the sob2D. And r(2D eob) equals the bifurcation radius at the first distal 2D eob.

Via the 3D model it is known which 2D centerline positions of the two image projections belong to which 3D centerline position. From a merged vessel, we then get two diameter measures per 3D position. These diameters are used as the lengths of the axis of an ellipse. In case there are more then two projections, the cross section area will be defined as the area of the object that is fitted by means of a spline through the corresponding nodes from the lumen wall contours from the 2D acquisitions.

The area of that ellipse is the cross-sectional area value we are interested in. This is block 31 of FIG. 7.

Figure 1:
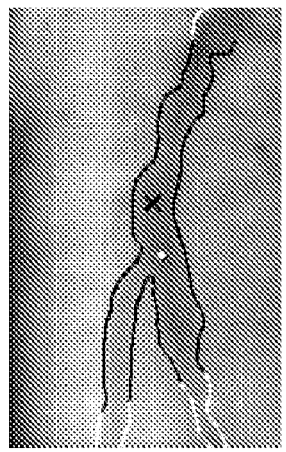
Figure 1:
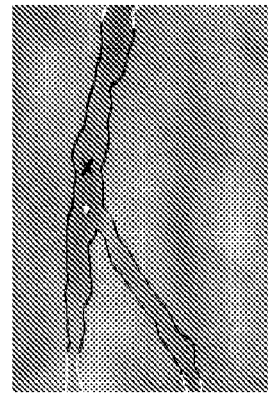
Figure 1:
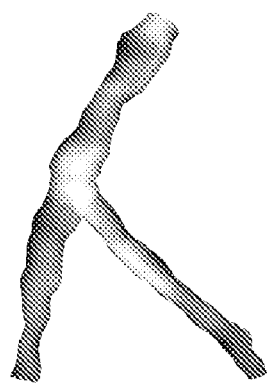
Figure 2:
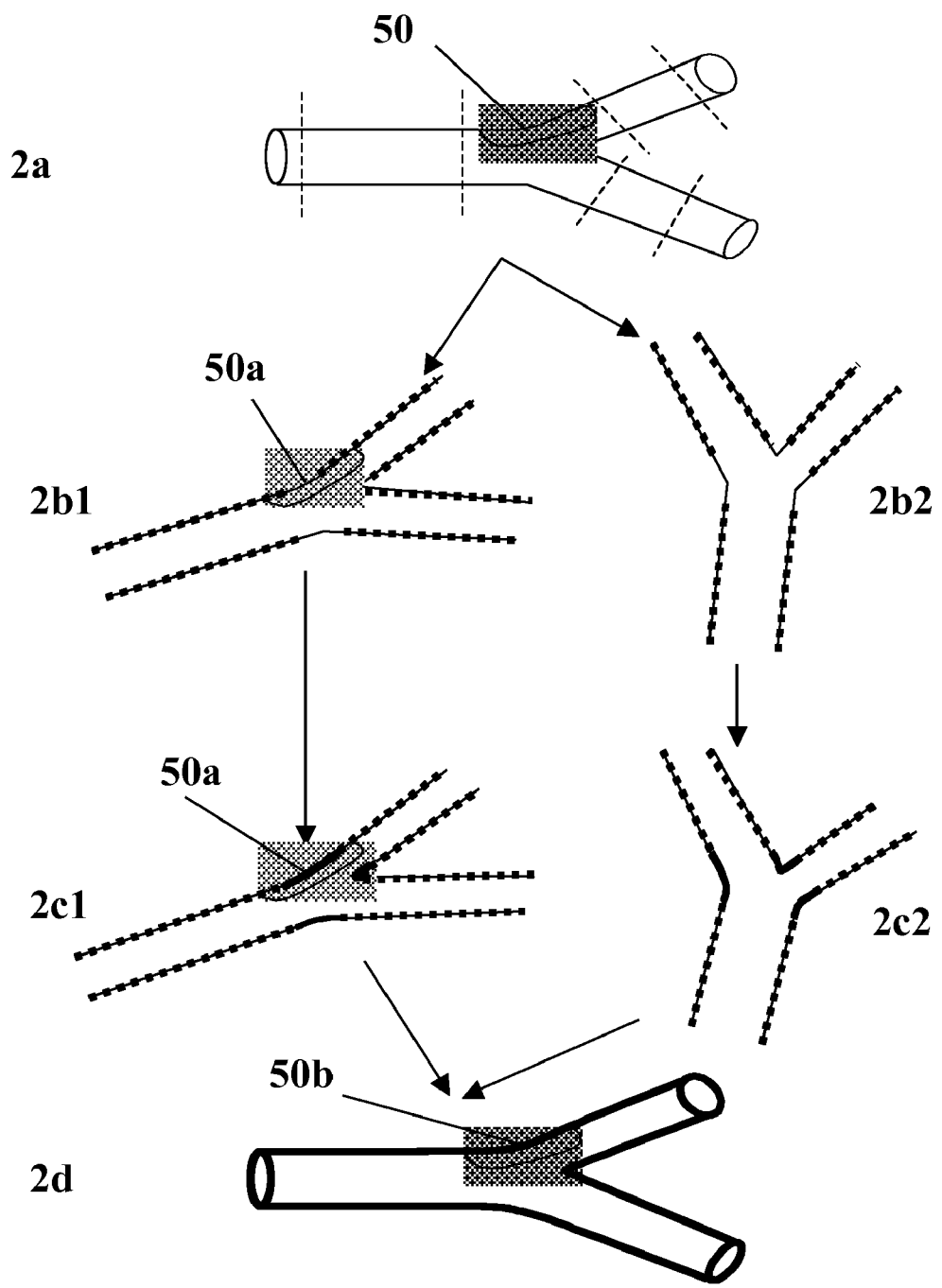

Now we describe the creation of the cross-sectional area curve in block 33 of FIG. 7 which is specified further by sub-blocks 35, 37, 39, 41. Block 33 is entered from block 31 through the call create reference area curve block 26. An example is shown in FIG. 2.

For the reference cross-sectional areas, a reconstruction of the healthy cross-sectional areas is made for each of the branches connected at the bifurcation (block 35 of FIG. 7). For this we use the 3D equivalent diameter curve as a detection diameter curve in a diameter reconstruction algorithm (for example, the diameter reconstruction algorithm described in Gronenschild et al, "A second Generation System for Off-line and On-line Quantitative Coronary Angiography", Catheterization and Cardiovascular Diagnosis 33:61-75 (1994), incorporated by reference herein in its entirety). In order to reconstruct the healthy cross-sectional areas, the obstruction extent must be available. The obstruction extent represents the artery part that is diseased. This problem is solved as follows:

If the obstruction extent is defined manually and it includes the bifurcation region, then we create a reconstruction using the non-obstructed regions of the artery In case no obstruction extent is known in advance in an artery, a healthy reconstruction using a single artery method (see, for example, the diameter reconstruction algorithm described in Gronenschild et al.) is made at the smallest absolute diameter in that artery.

This gives us a reference function in 3D for each of the three arteries connected at the bifurcation. The three functions together with the 3D obstruction borders (if available) are then mapped to 2D (block 37 of FIG. 7), which is trivial because the 3D model has a direct link to the 2D projections. The mapped information is used in the 2D bifurcation reconstruction algorithm as introduced in U.S. Ser. No. 11/845,154 to create the 2D healthy reconstructions of the bifurcation region (block 39 of FIG. 7). The 2D measurements are then combined into 3D measurements using a similar approach as for the 3D detection cross-sectional area function through the call create area curve 2 block 41. Note that the inputting to block 25 from blocks 24 and 41 lead to outputting towards blocks 26 and 28 respectively, as has been indicated by the lines 31*a* and 31*b* respectively.

The 3D obstruction extent is computed as the region defined by the positions closest to the lesion position with a relative diameter larger than 95%, ignoring the bifurcation region (here the relative diameter is the 3D detection diameter divided by the 3D reference diameter).

The lesion position is defined as the position with the smallest relative diameter from the diameter reference line for the main and side branch as explained by the second bullet above. Alternatively the lesion position is entered by a user person.

Figure 5:
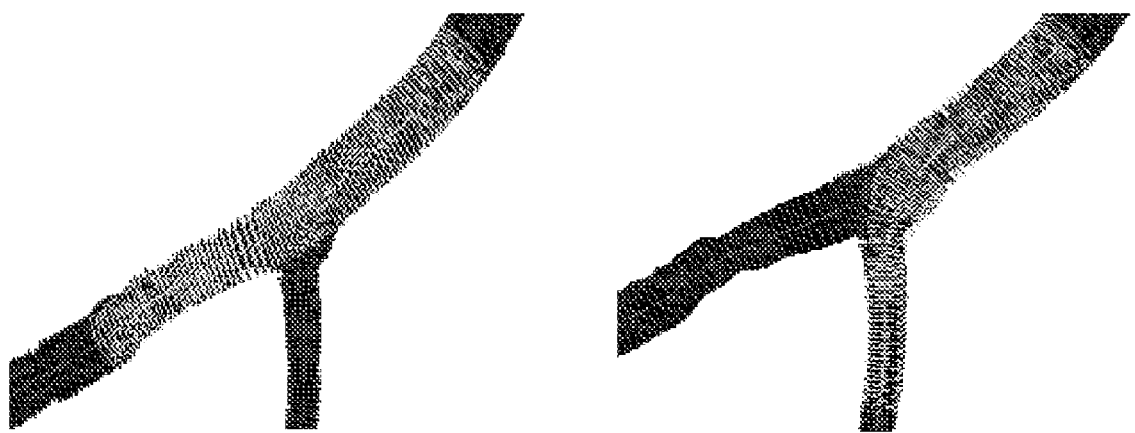
FIGS. 5a and 5b are 3D reconstructions of a bifurcation.
FIG. 5c is a 3D healthy model derived from the 3D reconstructions of the two branches as shown in FIGS. 5a and 5b. The healthy cross-sections are shown overlayed in white on the original diseased artery cross-sections in black.
Figure 5:
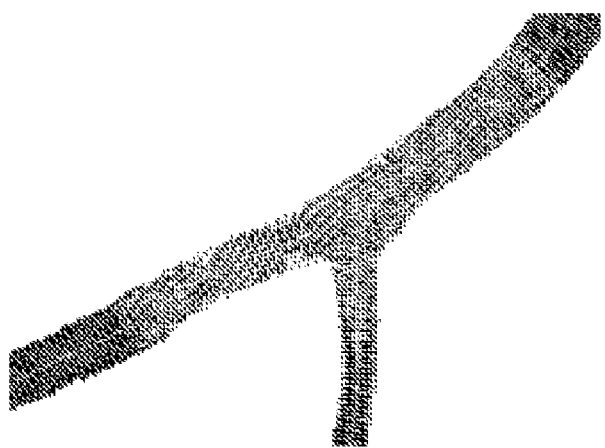

Now we will describe the creation of the healthy model (block 28 of FIG. 7). Based on the healthy cross-sectional areas of the bifurcation, obstruction boundaries and the diseased 3D model consisting of the bifurcation centerlines and cross-sections of the lumen on the centerline, the healthy centerline and cross-sections can be created. An example is shown in FIGS. 5*a* and 5*b*.

The 3D reconstructed centerlines for the main branch and side branch are then determined by fitting in an iterative process two splines within the obstruction borders by using a decreasing spline smoothing factor. This ensures that we first get a globally stable solution, before iterating to a solution that is locally optimum. Outside the obstruction borders, the bifurcation is assumed healthy and therefore, the reconstructed healthy centerline is identical to the original centerline.

We start by putting control nodes for the splines one diameter before and one diameter behind the obstruction borders plus a node at the point at which the proximal centerline splits into the first and second distal centerlines. This defines the initial centerlines for the main and side branches.

Hereafter we link each original centerline sample point to an associated point on the reconstructed centerline. This is done by determining the intersection from a plane (perpendicular to the original centerline through the original centerline point) with the reconstructed centerline. The point of intersection is the corresponding point.

We now have 3D centerlines for the main and side branches. We divide these two centerlines into three centerlines: the proximal, distal1 and distal2 centerline. The proximal centerline is the average of the two centerlines before the sample that corresponds to the split point of the original centerlines. The first and second distal centerline are respectively the main branch and side branch centerlines after that split point.

Because a healthy artery is substantially perfectly round, as is well known in anatomy, for each sample of the three reconstructed centerlines its cross-section can be expressed as a circle that is locally perpendicular to the centerline and has a midpoint equal to the centerline sample. The diameter of this circle then is the same as the equivalent healthy diameter.

Thereupon each circle is projected on the plane of the corresponding original cross-section of the unhealthy bifurcation. Note that this projected reconstruction circle is an ellipse. We then compute the displacement vector that defines how that ellipse must be moved, such that an as large part as possible of the original unhealthy sampled cross-sectional contour lies inside the ellipse. For each contour point of the original cross-section, it is determined whether that point is outside the ellipse and if so, how far the point lies outside the ellipse. The translation vector then equals the average of all vectors pointing from the ellipse origin to a contour point outside the ellipse. Each vector is weighted by the distance between the contour point and the ellipse.

The midpoint of the projected circle is then translated with the vector and serves as a new control node for our centerline splines in the next iteration of the iterative fitting process.

In order to minimize artifacts, no control node may be derived if the original and reconstruction planes differ by more than 30 angular degrees.

We now have a large set of new control nodes and theoretically, it is possible to have one control node for each centerline sample. However, this will give our spline a too large degree of local freedom (it will tend to be extremely noisy). To remedy this problem, groups of successive spline nodes are combined into an average control node if they are less than a local healthy equivalent diameter apart. If there are control nodes from multiple iterations present, only the control nodes from the latest iteration are used for producing the average.

The reconstructed centerlines are stable if there is no significant change in movement between successive iterations. We stop fitting if the movement of all centerline samples is at most an order of magnitude smaller than the resolution of the centerline.

In order to get a stable result, after the fifth iteration a control node is again added at the split point of the three reconstructed centerlines. In subsequent iterations, the combining of control node is slightly different. In a subset of successive spline nodes, that include the split point, instead of averaging the nodes in the set, the entire set is replaced by only the split point control node from the latest iteration.

We now have healthy models of both main and side branches consisting of the healthy centerline and circular cross-sections (see FIGS. 5a and 5b).These models must be merged into a single model of the bifurcation (see FIG. 5c).

Figure 6:
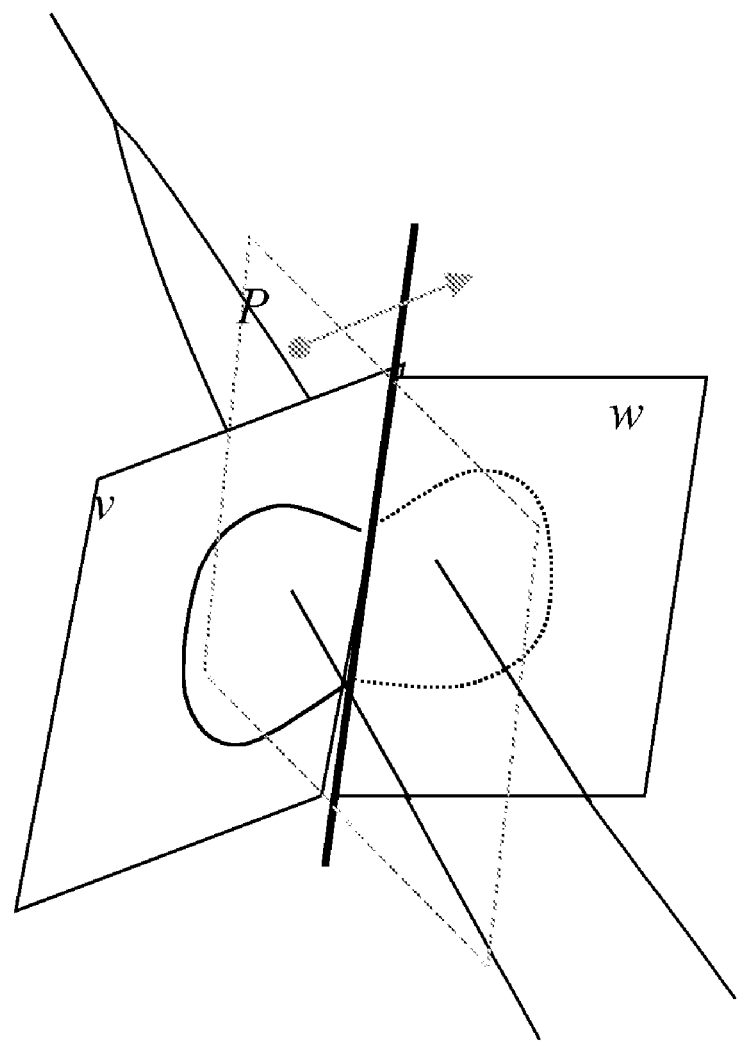
FIG. 6 is a pictorial illustration of clipping of two cross sections located in planes v and w, respectively; plane P is the plane through the intersection line of v and w, defined such that the difference in the angles between P and v and P and w is minimal; The sign of the normal to the plane always points to the side branch centerline; The points on the circular cross-sections that are on the wrong side of plane P are removed as shown in the Figure.

For this, first the circular cross-sections that make up the artery model are sampled for each of the three centerlines. Each distal2 cross-section is then clipped by a distal1 cross-section and via versa: For each distal1 cross-section i, the distal2 cross-section j is determined that maximizes the minimal amount of samples clipped away among cross-sections i and j. So now cross-section i and j form a pair. We compute j as follows:

We clip cross-section i by each distal cross-section h and vice versa and determine how many samples are clipped away in both cross-sections. We then take the minimum of the two values. If this minimum is maximal, then distal2 j equals h. Here it must however hold that if distal1 cross-section i-l is clipped by distal2 cross-section k then j≧k. The clipping of two cross-sections itself is depicted in FIG. 6.

The cross-section model is now transformed to a model of polylines by linking the samples of the successive cross-sections. For each tupel (pair) of successive cross-sections, first the two closest contour samples are connected by a line. Thereafter the remaining samples are connected by lines in sequential order.

Next, self-intersections of the main branch model and side branch model are computed. For each cross-section sample the result indicates whether the sample is valid or not. Note that the model between two successive cross-sections can be mathematically expressed as a clipped cone. So the finding whether a sample is invalid simplifies to finding whether the sample is in any of the clipped cones (we ignore the clipped cones that are made up from the cross-section on which the sample resides).

Of course, a proximal cross-section sample is invalid, if the main branch or side branch has a self-intersection at that sample.

Each invalid point on a poly-line is then replaced by a new point found by linear interpolation between the nearest valid point before and the first valid point after that invalid point on the polyline. The first and last cross-sections inside the obstruction are always assumed to consist of valid samples.

A special case is when a point of the cross-section at the pob is invalid. In this case, we interpolate between the last valid point before the pob and the first valid distal1 or distal2 cross-section point. We pick the distal1 point if it is not clipped away. Otherwise, we pick the distal2 point.

At last each clipped cross-section is linked seamlessly by straight lines to the cross-section it is clipped by for usage in model rendering: suppose cross-section v is clipped by cross-section w. Then we replace the end-points of the open contour of cross-section v by the end-points of cross-section w if and only if no other cross-section is clipped by v. Otherwise, we need to choose the opposite.

The clipped contours model is not only useful for visualization. From the model also the lumen volume within the bifurcation region can be computed: the volume of the region bounded by two successive main or side branch cross-sections equals the average area of the uncorrected clipped cross-sections, multiplied by the distance between the centerline points of the cross-sections.

The volume between the pob cross-section and the first distal1 cross-section needs however to be computed differently. It equals the average of half the area of the pob cross-section and the area of the clipped distal1 cross-section, multiplied by the distance between the centerline points of the cross-sections. Similarly, this holds for the side-branch vessel.

When the volumes between all main and side branch clipped cross-sections are added-up, the volume of the total bifurcation region is obtained.

For computation of the area of the clipped cross-sections, the un-sampled version of the cross-section is used. As the clipped cross-section is a circle clipped by a plane, there exists a closed formula for finding the area.

Note that a single non-bifurcated artery can be reconstructed via a modification of the above algorithm: in fact, this can be regarded as a reconstruction of the centerline and cross-sections of a single branch. The proximal centerline merging, pob placement and cross-section clipping are then left out. Otherwise, steps to be taken are the same.

The compute quantitative analysis block (block 30 of FIG. 7) will yield results to make the invention immediately applicable in various fields. A particular example of such implementation would be the use of the 3D equivalent (healthy) diameter in a 2D bifurcation analysis as introduced in U.S. application Ser. No. 11/845,154, incorporated by reference above.

A quantitative analysis result that is part of our method is the so called tortuosity. The tortuosity measure gives information about how tortuous (or curved) a particular vessel is. It can be measured over the bifurcation as well. In prior literature various attempts have been made to measure this tortuosity. See Bullitt et al, 2003, "Measuring Tortuosity of the intracerebral vasculature from MRA images", IEEE-TMI 22, pp 1163-1171, and Hart, Goldbaum, Cote, Kube, Nelson. Automated measurement of retinal vascular tortuosity. International Journal of Medical Informatics, Vol. 53, No. 2-3, p. 239-252, 1999, incorporated by reference herein in their entireties. However they all fail to capture the physiological perception of tortuosity. Secondly these methods cannot be generalized to 3D.

Instead, a novel determination is introduced here that reconstructs the centerline as it would look like with zero tortuosity. The result is a polyline P where the vertices of the polyline are placed at the positions of minimum curvature. The N vertices of the polyline divide the curve in N−1 sections. Our tortuosity measure then equals the sum of the detected length of each section divided by reconstructed (polyline) length minus one.

In our definition we look at the centerline of the vessel at scale s, where s equals the average equivalent diameter. In practice this means that the vessel centerline is smoothed with a gaussian kernel of that scale (which is a standard approach for measuring discrete functions like a sampled centerline).

Finding P: A centerline point $c(i)$ is a vertex of P if i is between the user defined borders AND $c(i)$ is located between two points of extreme curvature above a threshold t that have opposite curvature (sign) AND $c(i)$ is the local minimum in curvature between such two extrema. The centerline points at the boundaries of the region for which to measure the tortuosity are always included.

Threshold t is determined automatically. It equals the average noise level of the centerline at scale s. This is defined as the mean difference between that centerline and that centerline smoothed by a mean filter of the same size as the average equivalent diameter. Here the definition of 3D curvature is $k=|c'\times c''|/|c'|^3$ where c' and c'' are numerical approximations of the first and second-order derivative of the vessel centerline c.

We also need a definition for opposite curvature. For 2D curve, 'opposite curvature' means just that the sign of the curvature 'k' changes. For 3D curves, 'k' is always positive. However we do not need to have a global definition of curvature sign. So instead we compare how the curvature differs at the two extremes A and B we want to compare. This can be done by computing the angle between the normal vector at A and B on the centerline. If the angle is larger than PI/2 then the curve has swapped direction. Note that for a 2D curve, the two definitions of opposite curvature (i.e. sign of k and an angle larger than PI/2) are equal, which makes our definition sound.

Now, the invention has herein been described by means of preferred embodiments. However, persons skilled in the art would readily recognize various amendments and variations thereto. In consequence, the disclosure should be considered as illustrative rather than limiting, and no limitations to the invention should be construed other than such that are explicitly recited by the appended Claims.

The invention claimed is:

1. A method for analysis of a bifurcated tubular organ using multiple 2D angiographic images of the organ, said method comprising:
   a. Creating a first 3D model based on said images;
   b. Defining a bifurcation region regarding said first 3D model;
   c. Creating an area curve regarding said first 3D model, including
      c.1 deriving a 2D representation of the bifurcated tubular organ based upon said bifurcation region, said 2D representation defining a bifurcation including a main branch and two side branches,
      c.2 converting said 2D representation to define two respective vessels formed by splitting of the bifurcation,
      c.3 measuring various diameters regarding said respective vessels, and
      c.4 combining 2D quantities regarding said respective vessels;
   d. Creating a reference area curve regarding the bifurcated tubular organ whilst reconstructing in 2D;
   e. Creating a 3D healthy model of the bifurcated tubular organ based upon said area curves; and
   f. Computing quantitative analysis results regarding said 3D healthy model of the bifurcated tubular organ.

2. A method as claimed in claim 1, wherein:
   both said defining a bifurcation region of b and said creating a reference area curve of d include selecting respective instances of said creating an area curve of c.

3. A method as claimed in claim 1, wherein:
   said 3D healthy model of the bifurcated tubular organ is based upon said first 3D model, said first 3D model including at least one of centerlines for portions of said bifurcation region, circular cross-sectional areas of said bifurcation region along the centerlines, and obstruction boundaries.

4. A method as claimed in claim 1, wherein:
   said creating a reference area curve of d includes
      d.1 Reconstructing a single branch;
      d.2 Mapping said single branch reconstruction to 2D;
      d.3 Reconstructing the bifurcation region in 2D; and
      d.4 Creating an area curve regarding said reconstruction of d.3.

5. A method as claimed in claim 1, wherein:
the splitting of the bifurcation of c.2 that defines two respective vessels is effected by the step of defining a virtual edge for each respective vessel.

6. A method as claimed in claim 4, wherein:
said reconstructing of d.3 involves processing said images to identify contours of said organ, using said contours to determine a Polygon of Confluence amongst said organ, using said Polygon of Confluence to determine at least one parameter value characterizing geometry of said organ and outputting said parameter value to a user.

7. A method as claimed in claim 6, wherein:
at least one reference diameter is derived from a set of annuli with an inner circular edge fitted to an inner edge curve and an outer circular edge fitted to an opposite edge curve.

8. A method as claimed in claim 7, wherein:
at least one derived parameter comprises at least one reference diameter value for said bifurcation region, and said reference diameter compensating for damage to the bifurcation region.

9. A method as claimed in claim 8, wherein:
said at least one reference diameter value is selected from a group including a reference diameter for a proximal part of the bifurcation region, a reference diameter for a first distal part of the bifurcation region, and a reference diameter value for a second distal part of the bifurcation region.

10. A method as claimed in claim 1, wherein:
said 3D healthy model of the bifurcated tubular organ is based upon 3D reconstructed centerlines for a main branch and a side branch of the bifurcated tubular organ, the 3D reconstructed centerlines determined by an iterative process that fits two splines within obstruction borders using a decreasing spline smoothing factor.

11. A method as claimed in claim 1, further comprising:
computing a tortuosity measure as an indication of vessel quality.

12. A method as claimed in claim 4, wherein:
the reconstruction of d.1 is made by defining a region of the single branch that is healthy.

13. A method as claimed in claim 1, wherein:
the 3D healthy model of the bifurcated tubular organ is based upon obstruction boundaries that are automatically computed using the reference area curve of d.

14. A method as claimed in claim 1, further comprising:
computing a volume of the 3D healthy model of the bifurcated tubular organ.

15. A data processing facility for analysis of a bifurcated tubular organ using multiple 2D angiographic images of the organ, comprising:
means for creating a first 3D model based on said images;
means for defining a bifurcation region regarding said first 3D model;
means for creating an area curve regarding said first 3D model region, including
means for deriving a 2D representation of the bifurcated tubular organ based upon said bifurcation region, said 2D representation defining a bifurcation including a main branch and two side branches,
means for converting said 2D representation to define two respective vessels formed by splitting of the bifurcation,
means for measuring various diameters regarding said respective vessels, and
means for combining 2D quantities regarding said respective vessels;
means for creating a reference area curve regarding the bifurcated tubular organ whilst reconstructing in 2D;
means for creating a 3D healthy model of the bifurcated tubular organ based upon said area curves; and
means for computing quantitative analysis results regarding said 3D healthy model of the bifurcated tubular organ.

16. A non-transitory program storage device adapted for reading by a data processing machine, tangibly embodying a program of instructions executable by the machine to perform method steps for the quantitative analysis a medical image data of a bifurcated tubular organ, the method steps including the method as claimed in claim 1.

17. A data processing facility as claimed in claim 15, wherein:
said 3D healthy model of the bifurcated tubular organ is based upon said first 3D model, said first 3D model including at least one of centerlines for portions of said bifurcation region, circular cross-sectional areas of said bifurcation region along the centerlines, and obstruction boundaries.

* * * * *